United States Patent [19]

McIntosh

[11] Patent Number: 4,608,289
[45] Date of Patent: Aug. 26, 1986

[54] CARPET CONTAINING SANITIZING COMPOUNDS AND METHODS

[75] Inventor: Robert H. McIntosh, Greensboro, N.C.

[73] Assignee: Interface Research Corporation, Atlanta, Ga.

[21] Appl. No.: 570,952

[22] Filed: Mar. 8, 1984

Related U.S. Application Data

[63] Continuation of Ser. No. 523,734, Aug. 16, 1983, abandoned, which is a continuation of Ser. No. 226,006, Jan. 19, 1981, abandoned, which is a continuation of Ser. No. 149,555, May 13, 1980, abandoned, which is a continuation of Ser. No. 930,879, Aug. 4, 1978, abandoned.

[51] Int. Cl.⁴ .......................................... D03D 27/00
[52] U.S. Cl. ...................................... 428/95; 428/96; 428/97; 428/704
[58] Field of Search ................... 428/95, 96, 97, 704, 428/907

[56] References Cited

U.S. PATENT DOCUMENTS

| | | |
|---|---|---|
| 2,541,088 | 2/1951 | Nikawitz . |
| 2,676,122 | 4/1954 | McCarthy . |
| 2,891,878 | 6/1959 | Chamberlain .................... 117/138.8 |
| 2,970,081 | 1/1961 | McCall ................................ 167/30 |
| 3,247,134 | 4/1966 | Hwa . |
| 3,279,986 | 10/1966 | Hyman ................................ 167/42 |
| 3,280,131 | 10/1966 | Wakeman et al. .................. 260/286 |
| 3,308,488 | 5/1967 | Schoonman . |
| 3,364,192 | 1/1968 | Leach . |
| 3,705,235 | 12/1972 | McIntosh . |
| 3,762,415 | 8/1973 | Morrison . |
| 3,896,101 | 7/1975 | McIntosh . |
| 3,919,410 | 11/1975 | McIntosh . |
| 3,920,836 | 11/1975 | McIntosh . |
| 3,928,563 | 12/1975 | McIntosh . |
| 3,959,556 | 5/1976 | Morrison . |
| 4,024,324 | 5/1977 | Sparks . |
| 4,110,504 | 8/1978 | Hull . |
| 4,119,724 | 10/1948 | Thizy . |
| 4,259,078 | 3/1981 | Kleber . |
| 4,343,853 | 8/1982 | Morrison . |
| 4,401,712 | 8/1983 | Morrison . |
| 4,442,095 | 4/1984 | Johnston .......................... 424/248.5 |
| 4,442,096 | 4/1984 | Johnston .......................... 424/248.5 |

FOREIGN PATENT DOCUMENTS

| | | |
|---|---|---|
| 1162356 | 2/1984 | Canada . |
| 0035375 | 2/1981 | European Pat. Off. . |
| 2530584A1 | 7/1975 | Fed. Rep. of Germany . |
| 3014765A1 | 10/1981 | Fed. Rep. of Germany . |
| 3039437A1 | 5/1982 | Fed. Rep. of Germany . |
| 617854 | 12/1978 | Switzerland . |
| 1036578 | 8/1963 | United Kingdom . |

OTHER PUBLICATIONS

"Antimicrobials: Here to Stay or Just Another Fad?", Carpet & Rug Industry, Feb. 1984, pp. 8–14.
"Antimicrobial Activity on Carpet", Carpet & Rug Industry, Apr. 1984, pp. 22–27.
"Toxicants That Attack the Cell Wall", Microbiology of Cooling Water, James W. McCoy, 1980, Chemical Pub. Co. N.Y.

*Primary Examiner*—Marion C. McCamish
*Attorney, Agent, or Firm*—Jones & Askew

[57] ABSTRACT

The present invention consists of methods for using certain cationic alkyl phosphate derivatives as sanitizing agents in plastic materials for providing fungicidal and bactericidal properties which are effective against both Gram-positive and Gram-negative organisms including Pseudomonas aeruginosa. Various plastic materials of the invention are shown utilizing various sanitizing agents.

2 Claims, No Drawings

CARPET CONTAINING SANITIZING COMPOUNDS AND METHODS

This is a continuation of application Ser. No. 523,734 filed Aug. 16, 1983, now abandoned which was a continuation of application Ser. No. 226,006 filed Jan. 19, 1981, now abandoned which was a continuation of application Ser. No. 149,555 filed May 13, 1980, now abandoned which was a continuation of application Ser. No. 930,879 filed Aug. 4, 1978 also now abandoned.

BACKGROUND AND OBJECTIVES OF THE PRESENT INVENTION

Conventional plastic materials such as polyethylene, polyolifins, polyvinyl chlorides and other thermoplastic and thermosetting materials and other chemical structures such as acrylics and epoxies have conventionally had various additives introduced into their liquid state to provide sanitizing properties. For example, certain plastics have been rendered effective against gram-positive micro-organisms whereas other additives have been utilized to effectively kill Gram-negative organisms. Also, it has been conventional to combine the Gram-negative and Gram-positive bacteriostats to produce a plastic material whether sheet, film or a molded article that will inhibit the growth of both Gram-positive and Gram-negative organisms. However, various problems arise when introducing two additives into a plastic material in its molten or liquid state as the two component system may alter the physical properties of the plastic base material and the dual components must be tested to insure their compatibility and continued effective properties when combined into one plastic material. The relative strength and percentages of each of the components in the dual system must be measured and it is not uncommon to produce a plastic article which may initially have effective inhibiting properties for both Gram-negative and Gram-positive organisms whereupon later one or the other of the inhibiting additives will greatly lose its effectiveness while the other inhibiting additive remains effective. Also, since it is commonplace to mold, extrude, and otherwise subject the plastic base materials to high temperatures and temperature changes during forming or setting, it has been desirable to locate inhibitors which do not lose their effectiveness when subjected to high temperatures as are known within the plastic molding or forming arts.

With the disadvantages of the prior art additives in mind, it is an objective of the present invention to provide a single chemical compound which can be incorporated into plastic materials which will provide effective growth inhibition against both Gram-positive and Gram-negative organisms including *Pseudomonas aeruginosa*.

It is another object of the present invention to provide an effective inhibiting agent which can be subjected to the high temperatures of the plastic molding and forming art without losing its effectiveness and which remains effective for a long period of time.

It is still another objective of the present invention to provide a sanitizing agent which is relatively inexpensive and which requires no special handling procedures or techniques.

It is still another objective of the present invention to provide a sanitizing agent which can be incorporated in a low percentage into a wide range of plastic materials without adversely affecting the inherent properties of the plastic.

It is yet another objective of the present invention to provide a sanitizing agent which is effective against both Gram-positive and Gram-negative organisms over a wide percentage range.

It is also an objective of the present invention to provide a self-sanitizing plastic material which can be molded, cast, blown, extruded or calendared.

It is yet still another objective of the present invention to provide a plastic carpet backing which renders the upper carpet surface self-sanitizing.

SUMMARY OF THE INVENTION AND DESCRIPTION OF THE PREFERRED EMBODIMENT

It has been determined that certain alkyl phosphate derivatives can be dispersed into a liquid or molten plastic material to provide unique fungicidal and bactericidal properties to the plastic and sanitizing properties remain durable after the plastic material is molded, calendared, shaped or otherwise formed by methods known in the plastics forming art. The alkyl phosphate derivatives can be mixed into liquid polymers such as into polyvinyl chloride (PVC) dispersions, where, after fusion and calendaring takes place, the formed polyvinyl film or coating displays the unique bactericidal properties and is effective against both Gram-positive and Gram-negative orgamisms including *Pseudomonus aerginosa*. Other examples of plastic materials into which the alkyl phosphate derivatives of the present invention may find uses are polyethylene, cellulose acetate buterate, polyolefins, polypropylenes, polystyrene, various phenolic resins and polystyrene butadiene. Uses may also be found in epoxy, acrylic, polyvinyl acetate and other resins and polymeric emulsions. The amount of alkyl phosphate derivatives which are incorporated into the plastic mix can be varied depending on the particular use and the particular organisms which is sought to be inhibited. However, test results demonstrate that the alkyl phosphate derivative is generally sufficiently effective when less than one percent of the additive is used by weight of the weight of the plastic material. However, additive amounts of from one-hundredth percent (0.01%) to ten percent (10%) have been tried and have produced effective results under particular circumstances.

The alkyl phosphate derivatives of the present invention can be demonstrated by the general formula:

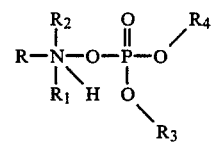

where
R = an alkyl group of up to 18 carbon atoms;
$R_1$ = —$CH_3$ or an a hydroxy substituted alkyl group of up to 18 carbon atoms;
$R_2 = R_1$;
$R_3$ = an alkyl group of up to 18 carbon atoms;
$R_4 = R_3$.

Examples of "R" values are shown in the chart below:

| R | R₁ | R₂ | R₃ | R₄ |
|---|---|---|---|---|
| $-C_xH_{2x+1}$ | $-CH_3$ $-C_xH_{2x}-OH$ | $-CH_3$ $-C_xH_{2x}-OH$ | $-C_xH_{2x+1}$ | $-C_xH_{2x+1}$ |
| where x = 1–18 | where x = 1–18 | where x = 1–18 | where x = 1–18 | where x = 1–18 |

The most preferred alkyl phosphate derivatives have been found to be:

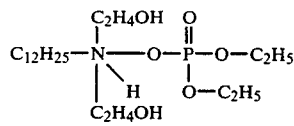

with the preferred amount being 0.10%–1% by weight based upon the weight of the plastic material to which it is added.

The present invention has been found to effectively inhibit the growth of both Gram-positive and Gram-negative organisms and has been determined to be effective against *Sarcina lutea, Staphylococcus aureus, Staphylococcus albus, Pseudomonas aeruginosa, Escherichia coli,* Klebsiella, *Candida albicans, Salmonella choleraesuis, Enterobacter aerogenes, Escherichia communior, Streptococcus pyogenes, Bacillus megaterium, Aspergillus niger,* and others.

When blending the selected additive into a plastic material an appropriate amount of the sanitizing agent or additive is selected. For example, if 1,000 pounds of polyethylene resin pellets are to be inhibited, 1 pound of the additive may be selected and added to a tumble mixing machine containing the polyethylene pellets. During the tumble mixing operation, the preferred embodiment of the additive as shown above forms an oily coating on the plastic pellets and as a result adheres to the pellets. After mixing for approximately fifteen minutes, the additive is homogeneously combined with the plastic polyethylene pellets, and as such, the coated pellets may be stored or shipped and there is no separation between the additive and the pellets. Again, this is a distinct advantage over the prior art systems where two or more additives are utilized to inhibit both Gram-positive and Gram-negative microorganisms since difficulty in mixing and separating has proven to be a serious disadvantage of prior art methods.

Liquid polymers, or polymer mixes, may also be utilized with the present invention although the plastic pellets or beads are the preferred form of plastic material for use in the present invention.

After the polyethylene pellets as above described have been sufficiently mixed with the selected additive, the pellets can then be charged to a hopper of a conventional melt extruder where the pellets are then melted and the sanitizing additive is homogeneously distributed throughout the melted mass by the action of the extruder. The resulting mass of plastic material may be formed in the desirable shapes, films or articles as is conventionally known. Sheets, or articles thus formed contain a uniform dispersion of the additive, and have a smooth, even texture.

During the heating in the melt extruder as mentioned above, temperatures may reach 250° C. although the preferable range is from 150° C.–250° C., although even at the higher temperatures no loss of effectiveness of the sanitizing agent is shown.

It is often desirable to utilize conventional spinerets in conjunction with melt extruders to form thermoplastic fibers. The present invention is adapted for use with such fiber formation and the threads and yarns which can be produced containing the inhibiting additive prevents both Gram-positive and Gram-negative organism growth on the yarns, threads and fabrics made therefrom.

An example of the utilization of the present invention will be described as follows:

One-tenth (0.1) to one and five-tenths (1.5) parts of the preferred embodiment (preferred alkyl phosphate derivative) are added to one hundred parts of polyethylene pellets of the sanitizing agent as demonstrated above. Pellets are coated with the oily additive by tumbling the mixture for twenty minutes. The pellets so treated are then fused in a test tube by emersing the test tube in an oil bath at 200° C. for twenty minutes. The test tube is then removed from the oil bath and allowed to cool to room temperature whereupon the molten mass solidifies. The cooled mass is then removed from the test tube and sawed into discs approximately 10 mm thick. No degradation or other unusual characteristics of the polyethylene discs are noted. The discs are placed in appropriately innoculated petri dishes containing nutrient agar. The agar thus innoculated with various organisms is allowed an incubation period of 24 hours at 37° C. with the discs present to inhibit the growth of the bacteria and fungi around the disc, whereupon a zone of inhibition is created. The results are as follows:

TABLE A

| ORGANISM | ZONE OF INHIBITION IN MM |
|---|---|
| *Staph-aureus* | 10 |
| *Pseudomonas Aeruginosa* | 4 |
| *E. Coli* | 6 |
| *Klebsiella* | 8 |
| *Candida albicans* | 10 |
| *Salmonella chloreasius* | 7 |
| *Aspergillus niger* | 10 |
| *Trichophyton mentagrophytes* | 15 |

It has been found particularly effective to form a self-sanitizing carpet by the addition of the sanitizing additives into the carpet backing during formation. Certain carpets utilize a polyvinyl chloride emulsion in the backing formation while other carpet manufacturers desire to coat the formed carpet with a resinous material such as styrene butadiene or other polymeric compositions. In either case, the sanitizing alkyl phosphate derivative can be incorporated into the backing during formation and as such provide a sanitizing agent for the carpet backing and the upper carpet surface due to the capillary action or attraction by the yarns of the carpet surface. This capillary action or attraction significantly reduces the Gram-positive and Gram-negative bacteria, including *Pseudomonas aeruginosa* which come in contact with the upper or lower surface of the carpet. Accordingly, if a nylon carpet is woven to which a styrene backing is thereafter applied by spraying or other methods which contains the alkyl phosphate additive, the nylon yarns or threads of the upper surface of the carpet, through capillary action, cause the additive which was mixed into the styrene butadiene to migrate towards the upper portions of the carpet surface and thereby form a carpet with a sanitizing effectiveness against a wide spectrum of common bacteria and fungi. As previously mentioned, various resins are utilized to form carpet backing and include polyvinyl chloride resins, styrene butadiene, polyolefins and others.

To determine the inhibitory effect of the preferred alkyl phosphate derivative:

$$C_{12}H_{25}-\underset{\underset{C_2H_4OH}{\overset{\diagdown}{H}}}{\overset{C_2H_4OH}{N}}-O-\underset{\underset{O-C_2H_5}{|}}{\overset{\overset{O}{\|}}{P}}-O-C_2H_5$$

of this invention of a carpet specimen on suitable test organisms, an applicable ASTM method (Designation: G22-67T) was used, which involved the following important steps:

(1) Specimen size of 100 nylon carpet yarns fused to a polyvinyl chloride backing was selected to measure 2×2 in.

(2) Test organisms were seeded in known concentrations (number of cells/ml) in nutrient salt agar media suitable for their growth. Each carpet specimen was sandwiched between layers of such inoculated agar media, in petri dishes—one for each organism. A total of 50-55 ml agar was used per petri dish.

(3) Specimen were incubated at 35°-37° C. (95° F. to 98.6° F.) for 12 days. Degree of inhibition on the growth of organisms was measured by the absence of bacterial growth.

(4) Observations for visible and physical effects in the specimen were made.

RESULTS (a) Microbial Inhibition

| Name of Organisms Used | Strength of Seeded Nutrient Salt Agar Media/ml | % of Total Number of Organisms Killed from Inoculum (Averaged from two trials) |
|---|---|---|
| Staphylococcus aureus | $18.5 \times 10^3$ | 100% |
| Escherichia coli | $10.2 \times 10^3$ | 99% |
| Bacillus megaterium | $13.6 \times 10^3$ | 99% |
| Pseudomonas aeruginosa | $16.3 \times 10^3$ | 99% |
| A. niger | | No growth |

(b) Physical changes in the carpet pieces

No microbial degradation of the carpet specimen was observed. There were no discoloration on washing and drying of the specimen at the end of 12 days incubation period.

Various other uses and modifications can be conceived and made by those skilled in the art and the examples as shown herein are not for the purpose of limiting this invention.

I claim:

1. A self-sanitizing, carpet product including thermoplastic surface yarn and a backing coat, said carpet product having an upper portion, and said backing coat including as a homogeneously distributed additive therein, an alkyl phosphate of the formula:

$$C_{12}H_{25}-\underset{\underset{C_2H_4OH}{\overset{\diagdown}{H}}}{\overset{C_2H_4OH}{N}}-O-\underset{\underset{O}{|}}{\overset{\overset{O}{\|}}{P}}\overset{R_4}{\underset{R_3}{\diagdown O}}$$

where:
$R_3$ = an alkyl group of up to 18 carbon atoms;
$R_4 = R_3$
said alkyl phosphate being present in said backing coat at a concentration of between 0.01% and 10% by weight based on the weight of said backing coat, and said backing coat being selected from the group consisting of a polyvinyl chloride emulsion and a styrene butadiene resin; and
said backing coat and said surface yarn being constructed and arranged so that alkyl phosphate in said backing coat will migrate by capillary action from said backing coat toward said upper portion of said carpet product to inhibit the growth of microorganisms therein.

2. Method of forming a self-sanitizing carpet product including thermoplastic surface yarn and a backing coat, wherein said carpet product has an upper portion, and said backing coat is selected from the group consisting of polyvinyl chloride emulsion and styrene butadiene resin, said method comprising emulsion and styrene butadiene resin, said method comprising the steps of:

a. homogeneously incorporating into said backing coat from 0.01% to 10% by weight based on the weight of said backing coat, an alkyl phosphate of the formula:

$$C_{12}H_{25}-\underset{\underset{C_2H_4OH}{\overset{\diagdown}{H}}}{\overset{C_2H_4OH}{N}}-O-\underset{\underset{O}{|}}{\overset{\overset{O}{\|}}{P}}\overset{R_4}{\underset{R_3}{\diagdown O}}$$

where:
$R_3$ = an alkyl group of up to 18 carbon atoms;
$R_4 = R_3$;

b. then applying said backing coat to said carpet product; and c. Permitting said alkyl phosphate additive to migrate by capillary action from said backing coat toward the upper portion of said carpet product to inhibit the growth of microorganisms therein.

* * * * *